United States Patent [19]

Schwartze et al.

[11] Patent Number: Plant 5,882

[45] Date of Patent: Feb. 17, 1987

[54] STRAWBERRY PLANT—SS484

[75] Inventors: Chester D. Schwartze, Puyallup, Wash; Atsusa Sakuma, deceased, late of LaConner, Wash., by Grace H. Sakuma, Executrix

[73] Assignee: Sakuma Bros. Farms, Inc., Burlington, Wash.

[21] Appl. No.: 641,497

[22] Filed: Aug. 16, 1984

[51] Int. Cl.[4] ..... A01H 5/03

[52] U.S. Cl. ..... Plt./49

[58] Field of Search ..... Plt./49

*Primary Examiner*—R. E. Bagwill

*Attorney, Agent, or Firm*—Hughes & Cassidy

[57] ABSTRACT

A new and distinct variety of day-neutral strawberry plant is characterized by its ability to produce fruit continuously and abundantly from June to October in western Washington, by superiority in this environment to available day-neutral and everbearing cultivars in characteristics that are especially valuable in garden culture, including fine flavor, continuous fruiting and sustained high productivity.

2 Drawing Figures

BACKGROUND OF THE NEW PLANT

This invention consists of a new and distinctive day-neutral strawberry cultivar designated SAKUMA. It originated as a seedling from a cross made in 1978 between the non-ever-bearing cultivar Tufts (U.S. Plant Pat. No. 3,561) and the day-neutral cultivar Tribute (formerly E.B.60), which is a non-patented plant originated by the U.S. Department of Agriculture at Beltsville, Md. from the cross E.B. 18 (MdUS 3082×Cal. 65.65.-601, day-neutral)×MdUS 4258.

Sakuma bore its fruit at Sakuma Bros. Farm, Inc., Burlington, Wash., was selected there and assigned selection No. SS484. Under this number it was tested and retested. In this environment it has been found superior in important fruit and plant characteristics as compared with Quinault which is the everbearing cultivar grown most widely in the Pacific Northwest. In less extensive comparisons it has been rated more highly than Ft. Laramie or Ozark Beauty or any of the more recently introduced everbearers including Aptos, Brighton, Hecker, Fern, Selva, Tillicum, Tribute and Tristar. All testing has been done under the assigned selection number.

Plants of Sakuma have been propagated asexually by use of runner plants separated from the original seedling plant and by multiplication of those runners plants. Typical runner plants were virus-indexed by standard methods and those that indexed virus-free were heat-treated to inactivate any remaining heat-labile virus and subsequently increased by meristem culture. Resulting plants were further increased by screenhouse propagation as required for certification by the Washington State Department of Agriculture.

(1) It is a slightly smaller plant than Ozark Beauty, Quinault, Selva or Burlington, having smaller leaves and shorter petioles than those varieties.

(2) It shows intensely day-neutral characteristics with rapid flowering of daughter plants even before they have rooted. Continuous flowering and fruiting of mother and daughter plants is exhibited in the field from June to October (at Burlington, Wash.).

(3) The nature and position of the clusters of flowers and fruits are relatively complex, somewhat like those of Tribute while much more so than those of Burlington, and often extend beyond or above the foliage during the summer months.

(4) Some clusters have subclusters with a primary fruit at the node from which the subclusters arise; the complexity results in rapidly diminishing size of flowers and fruits within the cluster.

(5) The size of the flower is moderate in comparison with Selva or Burlington, more nearly like the flower of Tribute.

Figure 2:
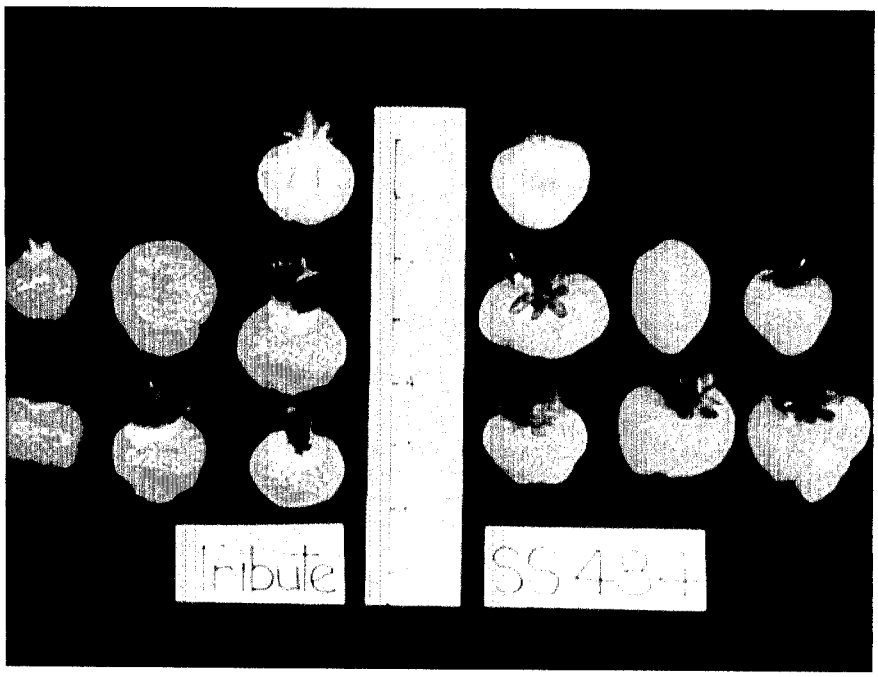
FIG. 2 provides a more detailed comparison of typical fruits of Sakuma (SS484) and Tribute, showing the more conic shapes, more uniform coloring and more flaring calyx of Sakuma.

(6) The shapes of the fruits are distinctive. On vigorous plants the largest primaries may be angular, even 3-sided, and measure as much as 2.5"D, 2.0" thick, 1.75"L; secondaries, somewhat smaller, are often broad-wedge to oblate-conic; tertiaries still smaller and usually conic. All shapes tend to be pointed toward the apex whereas Tribute fruits tend to be oblate, as best viewed in FIG. 2.

Figure 1:
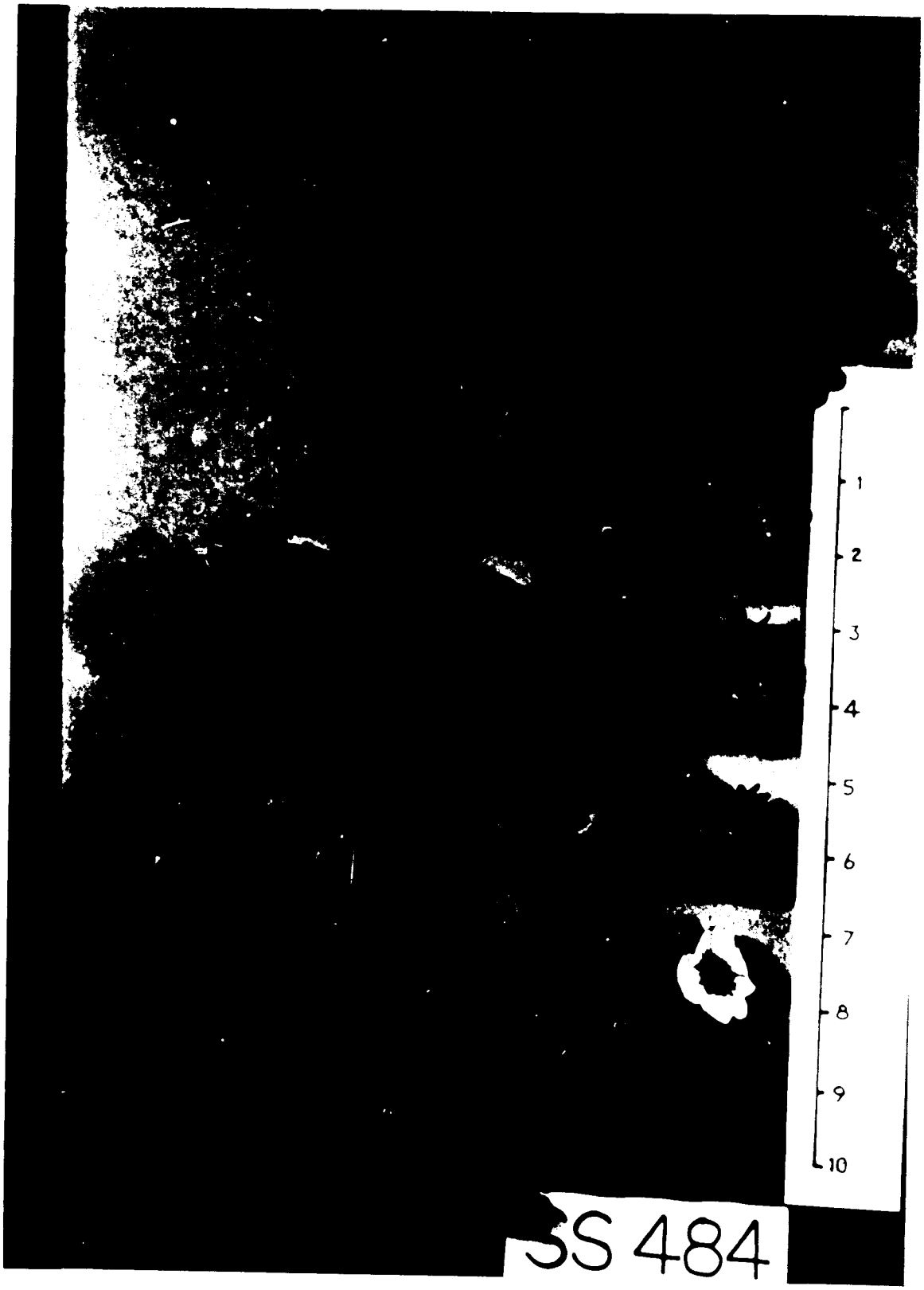
FIG. 1 shows the fullgrown plant in August on plastic mulch, with typical fruit clusters and also typical flower clusters, some extending above the foliage.

(7) The calyx (cap) is flat in smaller fruits, flared in larger ones, seldom reflexed; in very large fruits it may be imbedded. In contrast, the Tribute calyx is reflexed sharply upward around the stem, creating the appearance of a neck as best envisioned with reference to FIGS. 1 and 2.

(8) The absence of a white or red collar immediately below the stem of the fruit, a common occurrence with Tribute (FIG. 2) is a distinguishing feature of Sakuma.

(9) Other characteristics include slightly hollow fruits in Sakuma, less so than Tribute.

Skin color is light orange-red becoming medium orange-red and moderately glossy; skin color of Tribute is slightly darker and more glossy. Flesh color of the two is not significantly different. Flesh texture of Sakuma has been rated a little firmer and flavor sweeter than that of Tribute. Seeds of Sakuma are smaller and more yellow than those of Tribute; they are level with the surface whereas those of Tribute tend to be slightly raised.

In test plots Sakuma has been more productive than Ft. Laramie, Ozark Beauty or Quinault; in fruit quality, sweetness and palatability it has been rated superior to those cultivars.

Plants of Sakuma have shown excellent survival and exceptional uniformity of size and vigor throughout the test period. Occasionally a plant has succumbed to Verticillium Wilt. They have been infested and damaged moderately by Two-spotted Mite. Sakuma plants have shown strong resistance to powdery mildew. They have shown no virus symptoms when other selections and cultivars nearby have shown degenerative effects of common strawberry viruses.

Mulching with clear plastic has been beneficial, resulting in more vigorous growth, larger and cleaner berries, and yield increase approximating 50% in comparison with clean culture.

Because of its productivity, long season of ripening, relative freedom from plant diseases, and fine sweet flavor of the fruit, Sakuma appears to be especially well adapted to garden culture. Its parentage suggests that it may be adapted geographically beyond the Pacific Northwest.

What is claimed is:

1. A new and distinct variety of strawberry plant, as illustrated and described herein.

* * * * *